(12) United States Patent
Meshberg

(10) Patent No.: US 10,654,051 B2
(45) Date of Patent: May 19, 2020

(54) DROPLET DISPENSING ASSEMBLY AND CONVERTER ATTACHMENT FOR SPRAY-TO-DROPLET CONVERSION

(71) Applicant: Emil Meshberg, Fairfield, CT (US)

(72) Inventor: Emil Meshberg, Fairfield, CT (US)

(73) Assignee: Packaging Concepts Associates Holdings, Inc., Torrington, CT (US)

( * ) Notice: Subject to any disclaimer, the term of this patent is extended or adjusted under 35 U.S.C. 154(b) by 190 days.

(21) Appl. No.: 15/421,054

(22) Filed: Jan. 31, 2017

(65) Prior Publication Data

US 2018/0214894 A1 Aug. 2, 2018

(51) Int. Cl.
| | |
|---|---|
| *B05B 1/02* | (2006.01) |
| *B05B 11/00* | (2006.01) |
| *A61F 9/00* | (2006.01) |
| *A61M 11/00* | (2006.01) |
| *B05B 7/00* | (2006.01) |
| *B05B 1/26* | (2006.01) |
| *B05B 15/65* | (2018.01) |

(52) U.S. Cl.
CPC .................. *B05B 1/02* (2013.01); *A61F 9/00* (2013.01); *A61F 9/0008* (2013.01); *A61F 9/0026* (2013.01); *A61M 11/00* (2013.01); *B05B 1/265* (2013.01); *B05B 7/0012* (2013.01); *B05B 11/0089* (2013.01); *A61M 2210/0612* (2013.01); *B05B 11/3059* (2013.01); *B05B 15/65* (2018.02)

(58) Field of Classification Search
CPC ......... B05B 1/02; B05B 1/265; B05B 7/0092; B05B 11/0089; B05B 7/0012; B05B 15/65; B05B 11/3059; A61F 9/00; A61F 9/0008; A61F 9/0026; A01M 11/00; A61M 11/00; A61M 2210/0612
USPC ....... 239/333, 337, 343, 390, 391, 397, 432, 239/461, 499, 500, 504, 505, 507, 512, 239/521, 524, 542, 600
See application file for complete search history.

(56) References Cited

U.S. PATENT DOCUMENTS

| | | |
|---|---|---|
| 2,758,874 A | 8/1956 | Snyder |
| 2,968,441 A | 1/1961 | Holcomb |
| 3,058,670 A | 10/1962 | Marotto et al. |
| 4,611,759 A | 9/1986 | Cox |
| 4,706,663 A | 11/1987 | Makiej |
| 4,925,106 A * | 5/1990 | Maas .................. B05B 1/12 239/333 |
| 5,176,654 A | 1/1993 | Schreiber |

(Continued)

*Primary Examiner* — Steven J Ganey
(74) *Attorney, Agent, or Firm* — Glenn E. Gold, P.A.; Glenn E. Gold

(57) ABSTRACT

A droplet dispensing assembly includes a spray-to-droplet converter attachment, a cross wall, and a spray delivery tube. The converter attachment is a tubular wall with a passageway between its front and rear ends. The cross wall is disposed in the passageway, spaced from the tubular wall front and rear ends, and extends in a transverse relationship to, and connected with, the tubular wall to define an obstruction in a path of liquid travel through the passageway from the rear end to the front end such that liquid spray impacts the obstruction and converts into liquid droplets that are dispensed from the front end. The spray delivery tube has an exit end mated with the tubular wall upstream of the cross wall relative to the path of liquid travel through the passageway.

15 Claims, 10 Drawing Sheets

(56) References Cited

U.S. PATENT DOCUMENTS

| | | | |
|---|---|---|---|
| 5,678,765 A * | 10/1997 | Dobbs | B05B 7/0062 239/333 |
| 6,615,826 B1 | 9/2003 | Gabrio et al. | |
| 6,705,538 B2 * | 3/2004 | Fecht | B05B 7/0483 239/600 |
| 7,107,987 B2 | 9/2006 | Sundaram et al. | |
| 7,222,802 B2 * | 5/2007 | Sweeton | B05B 7/04 239/343 |
| 7,597,276 B2 | 10/2009 | Hawkins | |

* cited by examiner

DROPLET DISPENSING ASSEMBLY AND CONVERTER ATTACHMENT FOR SPRAY-TO-DROPLET CONVERSION

CROSS REFERENCE(S) TO RELATED APPLICATION(S)

This U.S. non-provisional utility patent application is related to U.S. non-provisional utility patent application Ser. No. 13/644,553, having a filing date of Oct. 4, 2012.

FIELD OF THE INVENTION

The present invention relates to spray dispensers, and, more particularly, is concerned with a droplet dispensing assembly and a converter attachment for spray-to-droplet conversion.

BACKGROUND OF THE INVENTION

Currently there are a number of liquid products being offered that are dispensed in either drop or spray form. For example, when a consumer looks for a treatment for an eye problem, such as for treating an eye irritation, he/she has the option to purchase a liquid product that can be sprayed into the eye or treated via drops dispensed from an eye dropper.

The consumer must decide on which option to go with before making the purchase. Currently, there is no liquid product being sold having a delivery system that permits the consumer to switch between applying the liquid product first in drop form and then next in spray form.

For consumers who prefer to purchase the liquid product in drop form, they are faced with the drawback that cross contamination may be experienced when using an eye dropper or pipette for dispensing the liquid product from a bottle. Each time the bottle is opened and the pipette removed to transfer the liquid product, the contents in the bottle may be contaminated by putting the pipette back inside the bottle.

Accordingly, there is a need in the art for an innovation that will overcome the deficiencies of the known art and the problems that remain unsolved.

SUMMARY OF THE INVENTION

The present invention is directed to an innovation that overcomes the deficiencies of the known art and the problems that remain unsolved by providing a droplet dispensing assembly and a spray-to-droplet converter attachment for spray-to-droplet conversion. The droplet dispensing assembly includes a spray delivery tube and the converter attachment which may be attached to or detached from the spray delivery tube depending on a consumer's preferred choice of delivery method (i.e., spray or droplets). Furthermore, contents of a bottle storing a liquid product is not contaminated since there is no need to open the bottle as would be the case in the use of a pipette.

In one aspect of the present invention, a spray-to-droplet converter attachment includes:
a tubular wall defining a passageway extending between opposite front and rear ends of the tubular wall; and
a cross wall disposed in the passageway and being spaced from the front and rear ends of the tubular wall and extending in a transverse relationship to, and connected with, the tubular wall so as to define an obstruction in a path of liquid travel through the passageway from the rear end to the front end of the tubular wall such that the liquid spray impacts the obstruction and converts into liquid droplets that are dispensed from the front end of the tubular wall.

In another aspect of the present invention, the tubular wall has a rearward wall portion defining a rear opening at the end of the tubular wall and an interior rear surface of an annular configuration on the rearward wall portion. The rear opening and interior rear surface define a socket end of the spray-to-droplet converter attachment, being located upstream of the cross wall relative to the path of liquid travel through the passageway, for receiving a complementary socket end of a spray delivery tube.

In another aspect of the present invention, the tubular wall also has a forward wall portion defining a front opening at the front end of the tubular wall and an interior front surface of annular configuration on the forward wall portion. The front opening and interior front surface define an outlet of the spray-to-droplet converter attachment, being located downstream of the cross wall relative to the path of liquid travel through the passageway, for dispensing liquid droplets from the spray-to-droplet converter attachment.

In another aspect of the present invention, the tubular wall further has an intermediate wall portion spaced from the front and rear ends of the tubular wall and extending between and interconnecting the rearward and front wall portions. The cross wall extends across the passageway and is connected with the intermediate wall portion of the tubular wall. The cross wall has an inner wall portion centrally located in the passageway so as to define the obstruction in the path of liquid travel through the passageway from the rear end to front end of the tubular wall. The cross wall also has an outer wall portion extending between and interconnecting the inner wall portion of the cross wall and the intermediate wall portion of the tubular wall so as to define space between the inner portion and the intermediate wall portion that enables the converted liquid droplets to move through the space past the inner portion of the cross wall, through the outlet of the converter attachment and beyond the front end of the tubular wall thereof.

In another aspect of the present invention, a droplet dispensing assembly includes:
a spray-to-droplet converter attachment having
a tubular wall of an annular configuration defining a passageway extending between opposite front and rear ends of the tubular wall, and
a cross wall disposed in the passageway and being spaced from the front and rear ends of the tubular, the cross wall extending in a transverse relationship to, and connected with, the tubular wall so as to define an obstruction in a path of liquid travel through the passageway from the rear end to the front end of the tubular wall such that liquid spray impacts the obstruction and converts into liquid droplets that are dispensed from the front end of the tubular wall downstream of the cross wall relative to the path of liquid travel through the tubular wall; and
a spray delivery tube having an exit end mated with the tubular wall of the spray-to-droplet converter attachment upstream of the cross wall thereof relative to the path of liquid travel through the passageway.

In another aspect of the present invention, a droplet dispensing assembly includes:
a spray-to-droplet converter attachment having
a tubular wall of an annular configuration defining a passageway extending between opposite front and rear ends of the tubular wall, the tubular wall having a rearward wall portion defining a rear opening at the rear end of the tubular wall and an interior rear surface of an annular configuration on the rearward wall portion, a forward wall portion defining a front opening at the front end of the tubular wall and an interior front surface of an annular configuration on the forward wall portion, and an intermediate wall portion spaced from the front and rear ends of the tubular wall, the intermediate wall portion extending between and interconnecting the rearward wall portion and the forward wall portion, and a cross wall of a planar configuration disposed in the passageway and being spaced from the front and rear ends of the tubular wall, the cross wall extending in a transverse relationship to, and connected with, the intermediate wall portion of the tubular wall so as to define an obstruction in a path of liquid travel through the passageway from the rear end to the front end of the tubular wall such that liquid spray impacts the obstruction and converts into liquid droplets that are dispensed from the front end of the tubular wall; and a spray delivery tube having a male socket exit end mated with the tubular wall of the spray-to-droplet converter attachment upstream of the cross wall thereof relative to the path of liquid travel through the passageway of the tubular wall;

wherein the rear opening and the interior rear surface of the rearward end portion of the tubular wall define a female socket end of the spray-to-droplet converter attachment, being located upstream of the cross wall relative to the path of liquid travel through the passageway, receiving the male socket exit end of the spray delivery tube;

also wherein the front opening and the interior front surface of the forward end portion of the tubular wall define an outlet of the spray-to-droplet converter attachment, being located downstream of the cross wall relative to the path of liquid travel through the passageway, for dispensing the converted liquid droplets from the spray-to-droplet converter attachment.

In another aspect of the present invention, the spray delivery tube is a nozzle extension having a nozzle at the exit end of the spray delivery tube that produces a liquid spray.

In another aspect of the present invention, the spray delivery tube comprises a nozzle extension having a nozzle at an entrance end of said spray delivery tube that produces a liquid spray.

These and other advantages of the invention will be further understood and appreciated by those skilled in the art by reference to the following written specification, claims and appended drawings.

BRIEF DESCRIPTION OF THE DRAWINGS

The components in the figures are not necessarily to scale, emphasis instead being placed upon illustrating the principles of the invention. The invention will now be described, by way of example, with reference to the accompanying drawings, in which.

In the figures, like reference numerals designate corresponding elements throughout the different views of the drawings.

DETAILED DESCRIPTION

Figure 1:
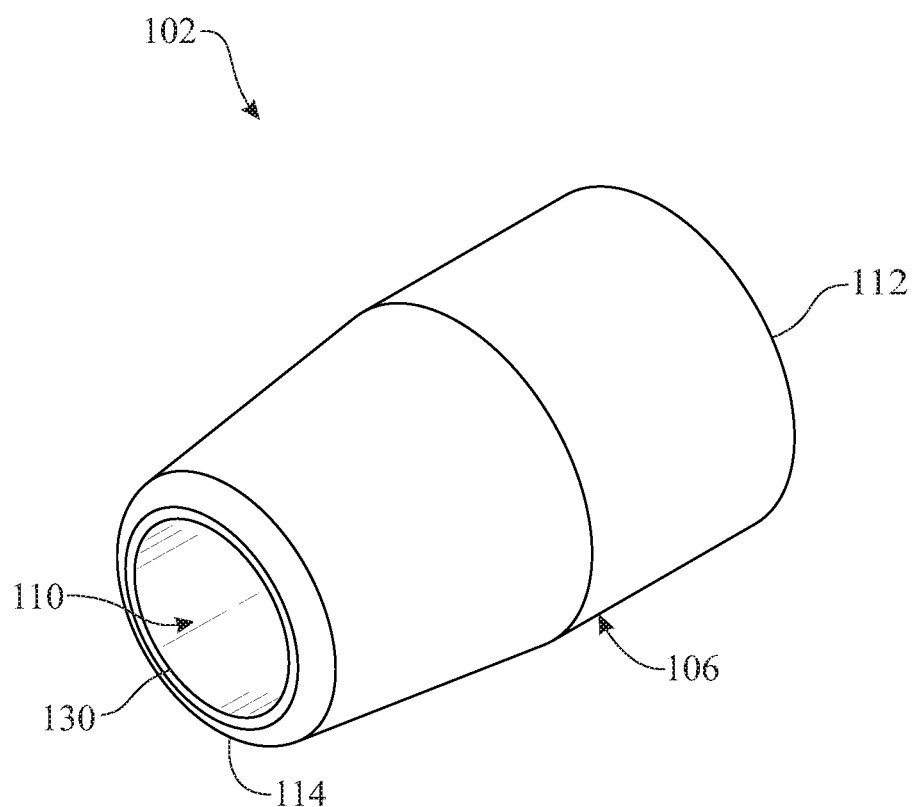
FIG. 1 presents a front isometric view of an exemplary embodiment of a spray-to-droplet converter attachment for a droplet dispensing assembly in accordance with aspects of the present invention.
Figure 2:
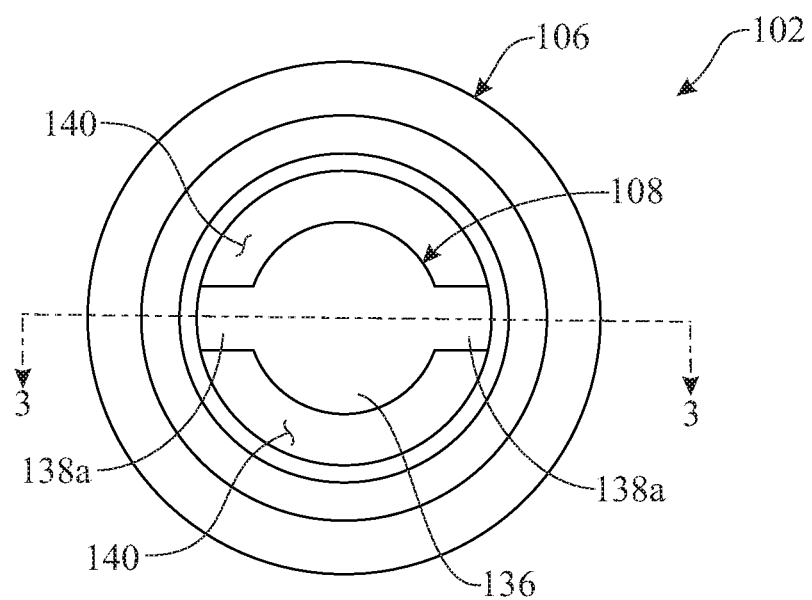
FIG. 2 presents a front plan view of the converter attachment as originally introduced in FIG. 1.
Figure 3:
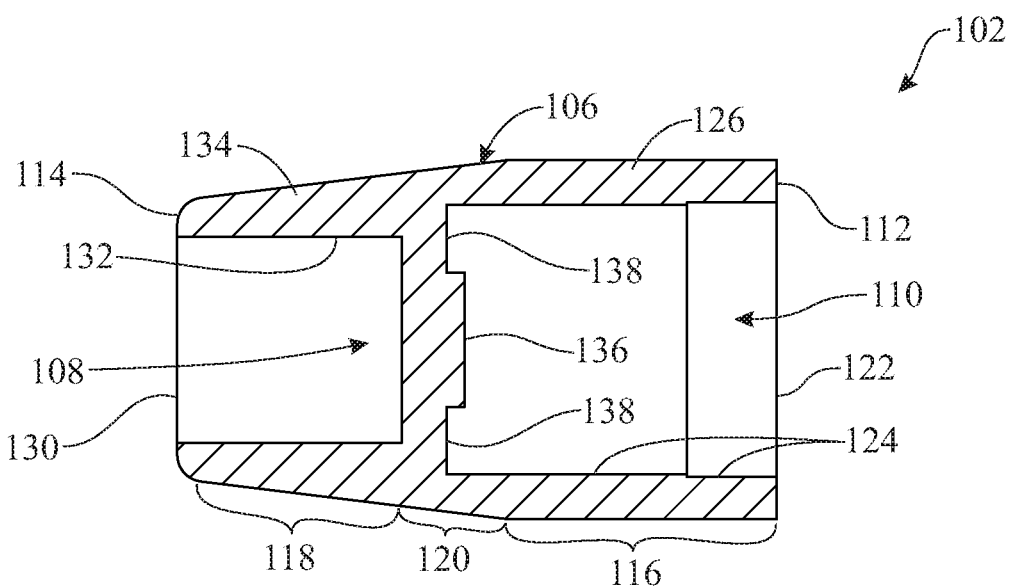
FIG. 3 presents a longitudinal sectional view of the converter attachment as seen along section line 3-3 in FIG. 2.
Figure 4:
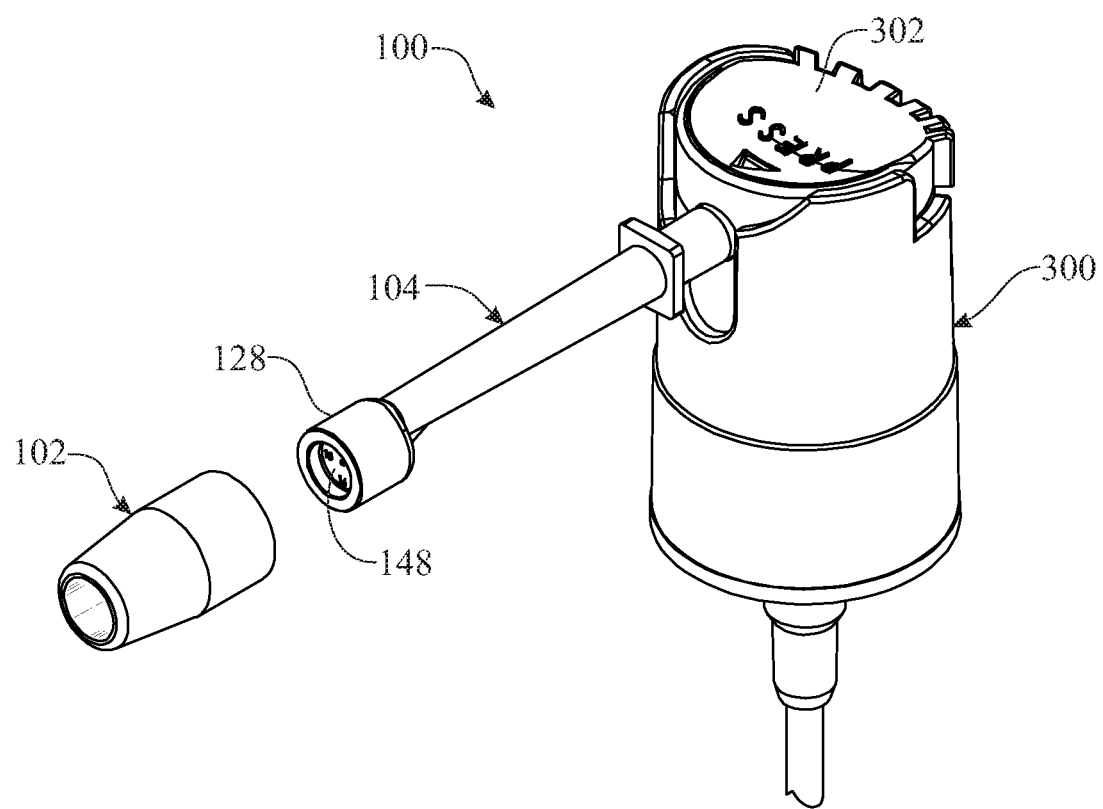
FIG. 4 presents a front isometric partially exploded view of an exemplary embodiment of a droplet dispensing assembly and the converter attachment as originally introduced in FIG. 1, illustrated with a child-restraint dispenser.
Figure 5:
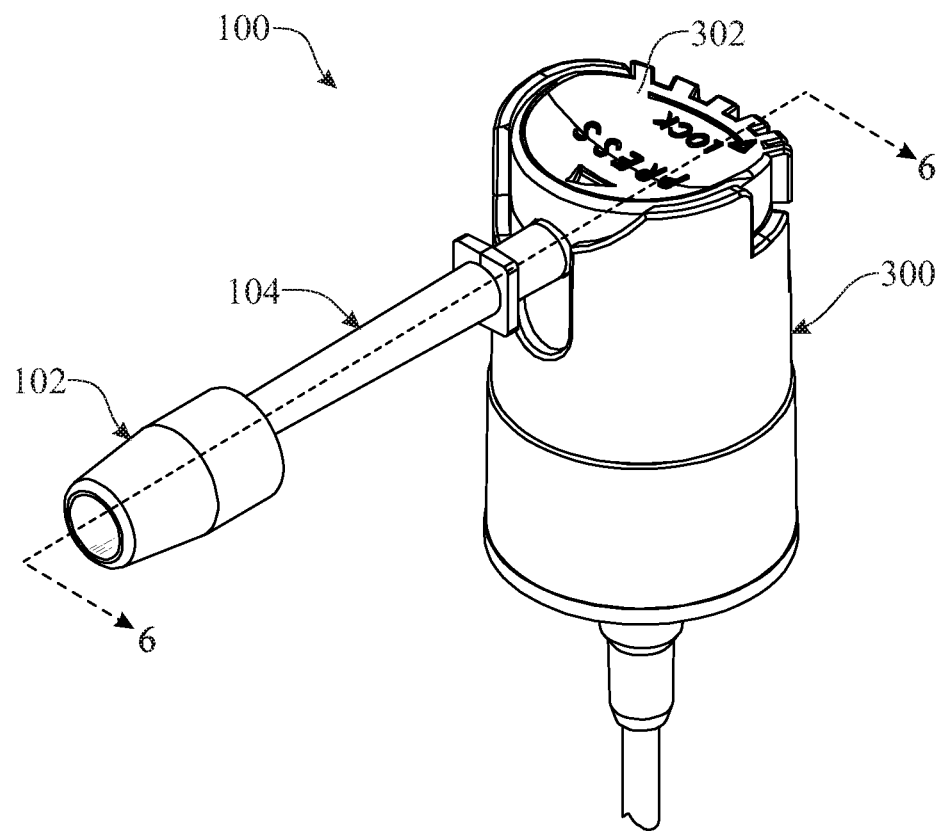
FIG. 5 presents a front isometric assembled view of the droplet dispensing assembly attached to the child-restraint dispenser.
Figure 6:
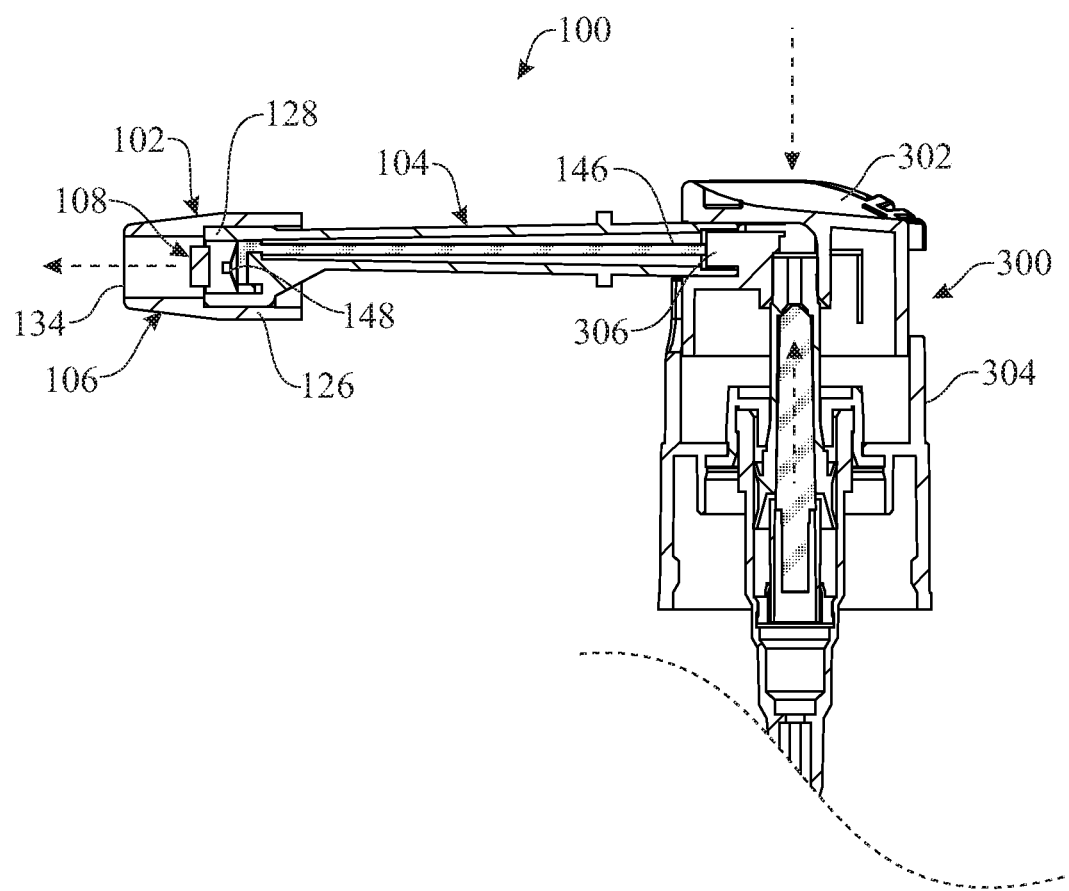
FIG. 6 presents a longitudinal sectional view of the droplet dispensing assembly attached to the child-restraint dispenser as taken along section line 6-6 of FIG. 5.
Figure 7:
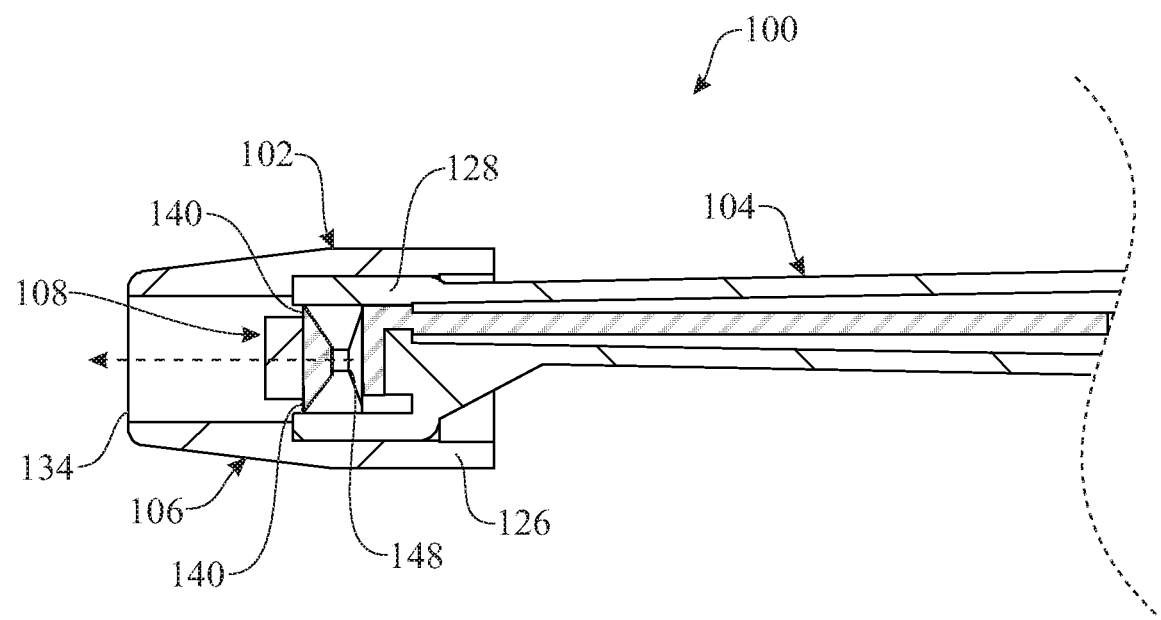
FIG. 7 presents an enlarged fragmentary view of the droplet dispensing assembly as illustrated in FIG. 6.
Figure 8:
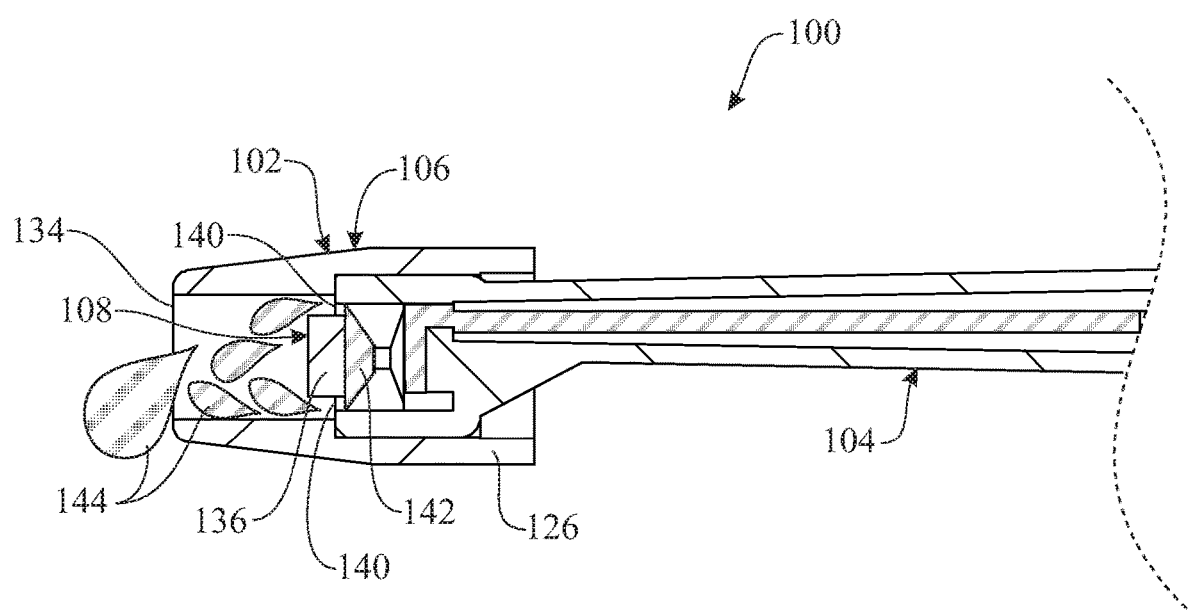
FIG. 8 presents an enlarged fragmentary view similar to that of FIG. 7 illustrating the conversion of the liquid product from spray to droplet form by the droplet dispensing assembly shown in FIG. 7.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. In other implementations, well-known features and methods have not been described in detail so as not to obscure the invention. For purposes of description herein, the terms "upper", "lower", "left", "right", "front", "back", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments that may be disclosed herein are not to be considered as limiting, unless the claims expressly state otherwise.

Referring now to FIGS. 1-11, there is illustrated an exemplary embodiment of a droplet dispensing assembly (FIGS. 4-11), generally designated 100, in accordance with aspects of the present invention. The droplet dispensing assembly 100 includes a spray-to-droplet converter attachment 102, as shown isolated from droplet dispensing assembly 100 in FIGS. 1-3. The spray-to-droplet converter attachment 102 may be seated upon a socket exit end 128 of a spray delivery tube 104, as shown in FIGS. 4-8. In other words, the distal end 128 of spray delivery tube 104 may be frictionally inserted into the spray-to-droplet converter attachment 102, such that a distal end of the spray delivery tube mates with the converter attachment 102.

More particularly, referring again to FIGS. 1-8, the spray-to-droplet converter attachment 102 of the droplet dispensing assembly 100 includes a tubular wall 106 of an annular configuration, and a cross wall 108 of a planar configuration. The tubular wall 106 of the spray-to-droplet converter attachment 102 has a passageway 110 extending between opposite rear and front ends 112, 114 of the tubular wall. The tubular wall 106 has a rearward wall portion 116, a forward wall portion 118, and an intermediate wall portion 120, all surrounding and defining the passageway 110. The intermediate wall portion 120 extends between and interconnects the rearward and forward wall portions 116, 118. The cross wall 108 of the spray-to-droplet converter attachment 102 is disposed in the passageway 110 and spaced from the rear and front ends 112, 114 of the tubular wall 106. The cross wall 108 extends across the passageway 110 in a transverse relationship to, and connected with, the intermediate wall portion 120 of the tubular wall 106.

The rearward wall portion 116 of the tubular wall 106 defines a rear opening 122 at the rear end 112 of the tubular wall and an interior rear surface 124 of an annular configuration on the rearward wall portion. The rear opening 122 and the interior rear surface 124 define a socket end 126 of the spray-to-droplet converter attachment 102, being located upstream of the cross wall 108 relative to the path of liquid travel through the passageway 110, for receiving a complementary socket exit end 128 of the spray delivery tube 104. The forward wall portion 118 of the tubular wall 106 defines a front opening 130 at the front end 114 of the tubular wall and an interior front surface 132 of an annular configuration on the forward wall portion. The front opening 130 and the interior front surface 132 define an outlet 134 of the spray-to-droplet converter attachment 102, being located downstream of the cross wall 108 relative to the path of liquid travel through the passageway 110, for dispensing liquid droplets from the spray-to-droplet converter attachment 102. Preferably, the interior rear surface 124 and the interior front surface 132 are both of cylindrical configuration, with the diameter of the interior rear surface 124 being greater than the diameter of the interior front surface 132.

The cross wall 108 has an inner wall portion 136, preferably of circular configuration, being centrally located in the passageway 110, and an outer wall portion 138 extending between, and interconnecting the inner wall portion 136 of the cross wall and the intermediate wall portion 120 of the tubular wall 106. The outer wall portion 138, which may take the form of a pair of spokes 138a disposed at opposite sides of the inner wall portion 136, supports the inner wall portion 136 at the central location within the passageway 110 so as to define an obstruction in a path of liquid travel through the passageway from the rearward wall portion 116 to the forward wall portion 118 of the tubular wall 106. The spokes 138a also define spaces 140 between the inner wall portion 136 of the cross wall 108 and the intermediate wall portion 120 of the tubular wall 106. Liquid spray 142 that impacts the cross wall 108 is converted into liquid droplets 144 which are enabled by the presence of the spaces 140 to travel or move through the spaces, past the inner wall portion 136 of the cross wall 108, and dispense from the outlet 134 of the spray-to-droplet converter attachment and beyond the front end 114 of the tubular wall 106 thereof.

Figure 9:
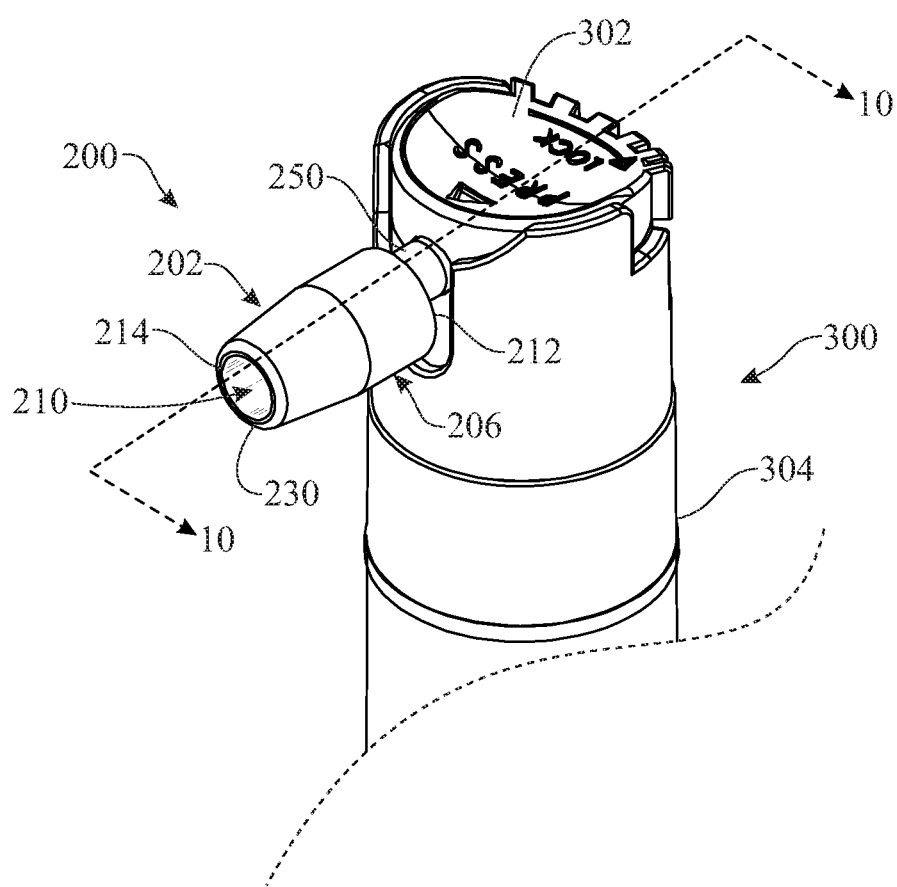
FIG. 9 presents a front isometric assembled view of another exemplary embodiment of a droplet dispensing assembly and the converter attachment as originally introduced in FIG. 1, illustrated attached to the child-restraint dispenser.
Figure 10:
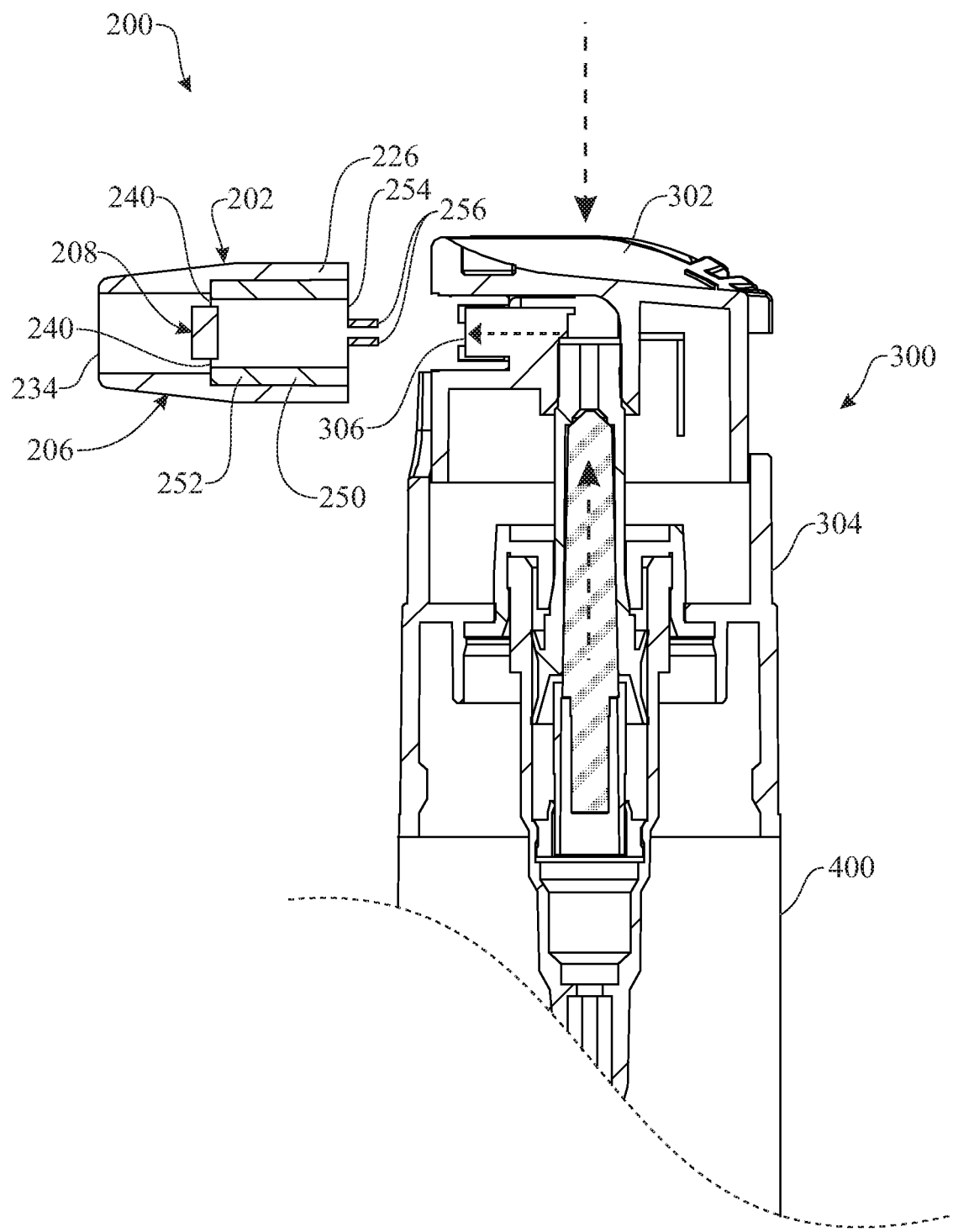
FIG. 10 presents a longitudinal sectional exploded view of the droplet dispenser assembly as taken along section line 10-10 of FIG. 9, but illustrated detached from the child-restraint dispenser.
Figure 11:
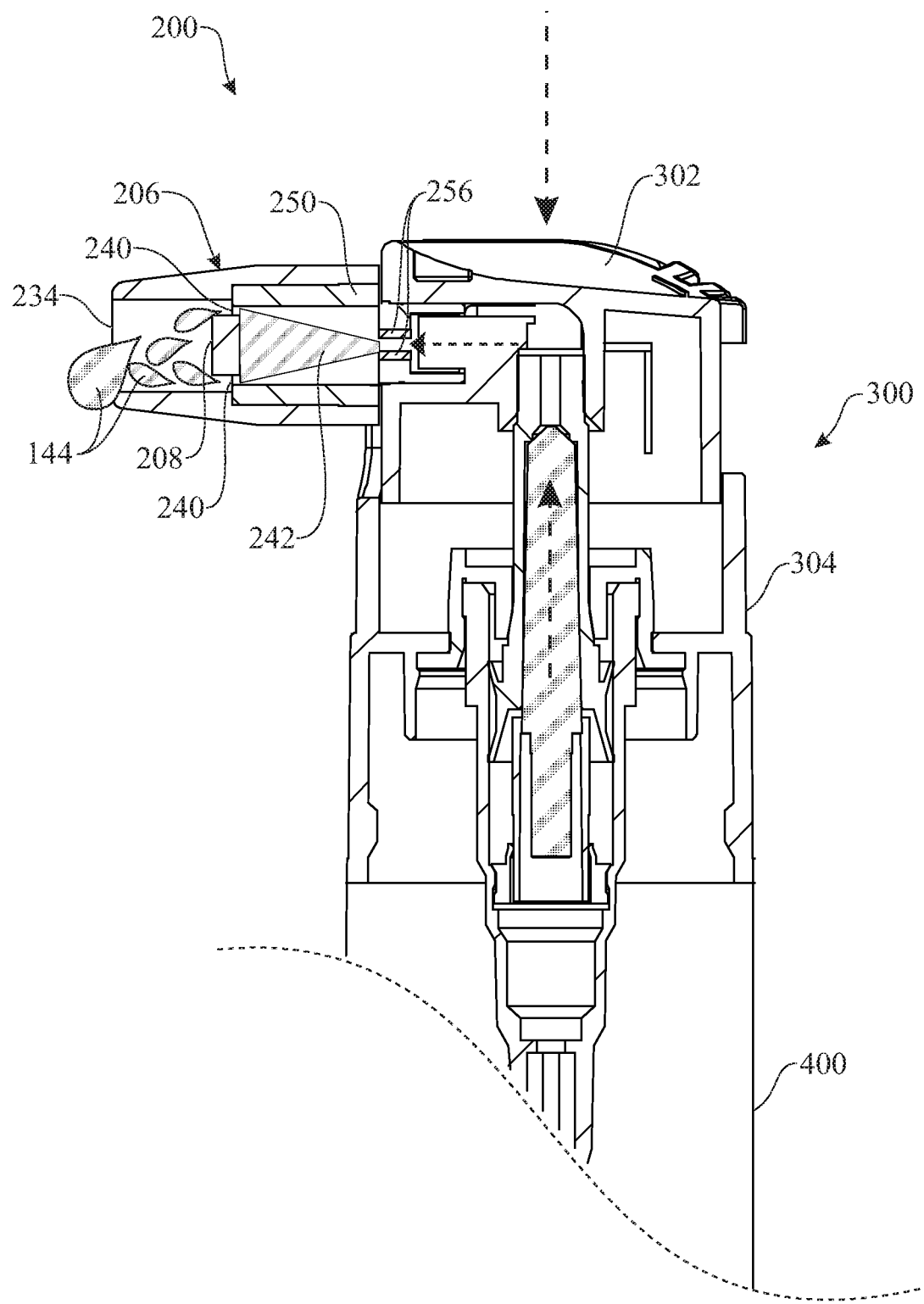
FIG. 11 presents a longitudinal sectional assembled view similar to that of FIG. 10 but illustrating the droplet dispenser assembly attached to the child-restraint dispenser and conversion of the liquid product from spray to droplet form by the droplet dispensing assembly shown in FIG. 10.

Referring to FIGS. 9-11, there is illustrated another exemplary embodiment of the droplet dispensing assembly, generally designated 200, in accordance with aspects of the present invention. The droplet dispensing assembly 200 includes a spray-to-droplet converter attachment 202, and a spray delivery tube 250 which mates with the converter attachment 202. The spray-to-droplet converter attachment 202 of the droplet dispensing assembly 200 is substantially identical to the spray-to-droplet converter attachment 102 and thus has the same parts designated by the same reference numerals except that the first digit of each reference numeral is "2" instead of "1".

Referring again to FIGS. 4-11, along with the droplet dispensing assemblies 100 and 200, there is illustrated a child-resistant dispenser 300 in the form of a safety closure used in conjunction with bottles containing potentially hazardous items to reduce the risk of children ingesting those items. However, it is readily understood that the spray-to-droplet converter attachment 102 can be assembled to a generic none child-resistant dispenser assembly. In FIGS. 4-8 the child-resistant dispenser 300 is one for assembling to a bottle (not shown) to form a child-resistant package. In FIGS. 9-11, the same child-resistant dispenser 300 is incorporated with a bottle 400 forming a child-resistant package. The bottle 400 is configured as a storage vessel defining a volumetric space therein capable of holding a defined volume or quantity of dispensable liquid product. Child-resistant packaging is required by regulation for prescription drugs, over-the-counter medications, pesticides, and household chemicals.

The child-resistant dispenser 300, comprising the invention of the patent application cross-referenced above, includes a dispensing actuator 302 disposed within a cap body 304 and configured for operation in two directions of motion: (1) a sliding motion along a longitudinal axis; and (2) a rotational motion about the longitudinal axis. As a result of these motions relative to the cap body 304, a dispensing mechanism 306 is actuated to dispense a liquid product stored within the container 400. The liquid product is dispensed from a discharge port 306 of the child-resistant dispenser 300 throughout the dispensing stroke of the dispensing actuator 302.

As shown in FIGS. 4-8, the spray delivery tube 104 of the droplet dispensing assembly 100, which mates at its male socket exit end 128 with the female socket end 126 of the spray-to-droplet converter attachment 102 of the droplet dispensing assembly, may take the form of a nozzle extension that mates at its entrance end 146 with the discharge port 306 of the child-resistant dispenser 300. The spray delivery tube/nozzle extension 104 may also include an atomizer nozzle 148 which produces the liquid spray 142 at the male socket exit end 128 and is in fluid communication with the passageway 110 of the spray-to-droplet converter attachment 102. The spray delivery tube 104 may have various annular cross-sectional configurations, such as cylindrical, square, rectangular, or oval.

As shown in FIGS. 9-11, the spray delivery tube 250 of the droplet dispensing assembly 200, which mates at its male socket exit end 252 with the female socket end 226 of the spray-to-droplet converter attachment 202 and is in communication with its passageway 110, may take the form of a nozzle extension that mates at its entrance end 254 with the discharge port 306 of the child-resistant dispenser 300 by means of a pair of closely-spaced tabs 256 which also function as a spray-producing nozzle.

The spray-to-droplet converter attachment 102, 202 can be fabricated so as to be removably attachable to, or in unitary construction with, any generic sprayer that has a spray delivery tube 104, 250. The spray-to-droplet converter attachment 102, 202 can also be selectively attachable to a generic sprayer not having a spray delivery tube 104, 250. The droplet dispensing assembly 100, 200 and the child-resistant dispenser 300 may be manufactured using any of various manufacturing processes well-known by those skilled in the art, including injection molding, vacuum forming, machining, and the like. Additionally, it is contemplated that the material selected to fabricate these components may be chosen based upon material properties that provide specific performance of each component for each respective function. It is also recognized that these components may be fabricated in different colors for any of a multitude of reasons, such as color-coding features and functionality, and the like.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A spray-to-droplet converter attachment configured for selective coupling to a distal end of a spray delivery tube, the spray delivery tube coupled at an opposite proximal end to a liquid spray source, the spray-to-droplet converter comprising:
   a contiguous tubular sidewall generally symmetrical about a central axis and defining a passageway extending between opposite front and rear open ends thereof, the tubular sidewall having a rearward wall portion defining both a rear opening at the tubular sidewall rear open end and an annular interior rear surface of the tubular sidewall rearward portion, the rear opening and the interior rear surface, together, defining a socket end of the spray-to-droplet converter attachment for receiving a complementary socket end of the spray delivery tube; and
   an interior cross-wall contiguous with the tubular sidewall and located downstream of the socket end of the spray-to-droplet converter attachment relative to a direction of travel of liquid through through the tubular sidewall passageway, the interior cross-wall disposed within the passageway between the front and rear ends of the tubular sidewall, the interior cross-wall extending in a transverse relationship to the tubular sidewall to define an obstruction along a path of liquid traveling through the passageway, in a direction from the rear end of the tubular sidewall to the front end of the tubular sidewall, in such a manner that a volume of liquid spray impacting the obstruction is converted into liquid droplets dispensed from the front end of the tubular sidewall.

2. The attachment of claim 1 wherein the tubular sidewall further comprises a forward wall portion defining both a front opening at the front end of the tubular sidewall and an annular interior front surface of the forward wall portion, the front opening and the interior front surface, together, defining a spray-to-droplet converter attachment outlet, located downstream of the cross-wall relative to the path of liquid travel through the passageway, for dispensing liquid droplets from the spray-to-droplet converter attachment.

3. The attachment of claim 1 wherein the tubular sidewall further comprises an intermediate wall portion between the front and rear ends of the tubular sidewall.

4. The attachment of claim 3 wherein the cross-wall extends across the passageway and is connected to the intermediate wall portion of the tubular sidewall.

5. The attachment of claim 4 wherein the cross-wall further comprises an inner wall portion centrally located within the passageway.

6. The attachment of claim 5 wherein the cross-wall further comprises an outer wall portion extending between and interconnecting the inner wall portion of the cross-wall and the intermediate wall portion of the tubular sidewall, thereby defining a space between the inner wall portion and the intermediate wall portion to enable communication of the converted liquid droplets through the space, past the inner wall portion of said cross-wall, and toward the front end of the tubular sidewall.

7. The attachment of claim 6 wherein said tubular sidewall further comprises a rearward wall portion defining a rear opening at the rear end of the tubular sidewall, and an annular interior rear surface of the rearward wall portion, the rear opening and the interior rear surface, together, defining a female-configured socket end of the spray-to-droplet converter attachment for receiving a male socket end of the spray delivery tube.

8. The attachment of claim 7 wherein the tubular sidewall further comprises a forward wall portion defining a front opening at the front end of the tubular sidewall, and an annular interior front surface of the forward wall portion, the front opening and the interior front surface, together, defining a spray-to-droplet converter attachment outlet, located downstream of the cross-wall relative to the path of liquid traveling through the passageway, for dispensing the converted liquid droplets from the spray-to-droplet converter attachment.

9. The attachment of claim 8, wherein the intermediate wall portion of the tubular sidewall extends between and interconnects the rearward and forward wall portions of the tubular sidewall.

10. A droplet dispensing assembly, comprising:
    a spray-to-droplet converter attachment comprising
        an annular tubular sidewall defining a passageway extending between opposite front and rear ends thereof, the tubular sidewall including a rearward wall portion defining a rear opening at the tubular sidewall rear end and an annular interior rear surface of the rearward wall portion, the rear opening and the annular interior rear surface, together, defining a female socket end of the spray-to-droplet converter attachment, and
        a cross-wall disposed in the passageway between the front and rear ends of the tubular sidewall, the cross-wall extending in a transverse relationship to, and connected with, the tubular sidewall to define an obstruction along a path of liquid traveling through the passageway in a direction from the rear end of the tubular sidewall to the front end of the tubular sidewall, such that liquid spray impacting the obstruction is converted into liquid droplets that are dispensed from the front end of the tubular sidewall; and a spray delivery tube having an exit end mated with the tubular sidewall upstream of the cross-wall relative to a direction of travel of liquid communicated through the passageway during operation of the droplet dispensing assembly, the female socket end located downstream of the cross-wall and configured for receiving a male socket on the exit end of the spray delivery tube.

11. The assembly of claim 10 wherein the tubular sidewall of the spray-to-droplet converter attachment further comprises a forward wall portion defining both a front opening at the front end of the tubular sidewall and an annular interior front surface of the forward wall portion, the front opening and the interior front surface, together, defining a spray-to-droplet converter attachment outlet.

12. The assembly of claim 11 wherein the tubular sidewall of said spray-to-droplet converter attachment further comprises an intermediate wall portion spaced inwardly from both the front and rear ends of the tubular sidewall.

13. The assembly of claim 12 wherein said cross-wall of the spray-to-droplet converter attachment spans the passageway and is integral with the intermediate wall portion.

14. The assembly of claim 13 wherein the cross-wall of the spray-to-droplet converter attachment further comprises an inner wall portion centrally located along the passageway to define said obstruction.

15. The assembly of claim 14 wherein the cross-wall further comprises an outer wall portion extending between and interconnecting the inner wall portion of the cross-wall and the intermediate wall portion of the tubular sidewall.

* * * * *